US00PP09269P

United States Patent [19]

Jessel, Jr.

[11] Patent Number: Plant 9,269

[45] Date of Patent: Aug. 29, 1995

[54] CARNATION PLANT NAMED 'CFPC FRESCO'

[75] Inventor: Walter H. Jessel, Jr., Salinas, Calif.

[73] Assignee: California Florida Plant Co., L.P., Salinas, Calif.

[21] Appl. No.: 315,135

[22] Filed: Sep. 29, 1994

[51] Int. Cl.[6] ..... A01H 5/00

[52] U.S. Cl. ..... Plt./70.7

[58] Field of Search ..... Plt. 70.7

*Primary Examiner*—James R. Feyrer

*Attorney, Agent, or Firm*—Christie, Parker & Hale

[57] ABSTRACT

A new dwarf carnation plant suitable for growing in pots producing flowers of red coloration.

1 Drawing Sheet

SUMMARY OF THE INVENTION

The present invention relates to a new and distinct dwarf variety of carnation plant which was originated by me in a controlled breeding program by my crossing as seed and pollen parents, two proprietary, unnamed and unpatented seedlings of my creation. The varietal denomination of this new carnation is 'CFPC Fresco'.

Among the novel combination of characteristics possessed by the new variety which distinguishes it are dwarf growth habit not requiring application of growth retardants tolerance to temperatures as high as 120° F. and as low as 10° F. and ability to produce flower buds that will open in a home environment with moderate light conditions. Flowers of the new variety are of an attractive red coloration.

Asexual reproduction by propagation by side shoot cuttings of the new variety as performed in Salinas, Calif., shows that the foregoing and other distinguishing characteristics come true to form and are established and transmitted through succeeding propagations.

Unlike preceding pot carnations, i.e., Lillipots (Sakata), Rocky Mountain Series (Goldsbury C.S.U.), and Knight Series (Goldsmith Seed Co.), CFPC pot carnations were selected and bred from indoor cut-types and are best grown under cover. The Lillipots etc. were bred from outdoor garden-types and species and are best grown outdoors. The CFPC pot varieties are dwarf due to a homozygous recessive dwarfing gene. If crossed to the aforementioned "pot-types", the resultant progeny returns to tall cut seedings.

The Lillipots and Knight Series are seed crops. The Rocky Mountain and European pot varieties (cuttings) are no longer commercially available.

BRIEF DESCRIPTION OF ILLUSTRATION

The accompanying illustration shows typical specimens of the vegetative growth and flowers of the new variety depicted in color as nearly true as it is reasonably possible to make the same in a color illustration of this character. Although propagation by side shoot cuttings is described, other known methods of asexual reproduction may also be used to reproduce 'CFPC Fresco'.

DESCRIPTION OF THE NEW VARIETY

The following is a detailed description of my new variety, with color terminology in accordance with the Royal Horitcultural Society Color Chart (RHSCC). The terminology used in color description herein refers to plate numbers in the aforementioned color chart.

Color designations and color descriptions may deviate from the stated values depending upon varying environmental, seasonal and cultural conditions.

The information provided herein is based on observations of plants grown inside commercial greenhouses at Salinas, Calif. The height of plant and flower and foliage size are established as an average using standard commercial cultural practices. Where general terms such as average, normal, ordinary, etc. are used, characteristics so described are not considered distinguishing.

Name: CFPC Fresco.

Classification:

*Botanical.*—*Dianthus caryophyllus.*

*Commercial.*—Carnation, dwarf pot type.

Parentage:

*Female parent.*—Unnamed seedling (No. 890354).

*Male parent.*—Unnamed seeding (No. 890397).

Plant:

*Height.*—About 8 inches.

*Growing habit.*—Herbaceous, semi-upright, pot type.

*Blooming habit.*—As a spray.

*Blooming season.*—Year round.

*Rooting time.*—About 13 days.

*Mutation prone.*—No.

*Disease resistance.*—Good.

*Temperature tolerance.*—120° F. to 10° F.

*Breaking action.*—Good, average number 5.

Foliage:

*Color.*—Upper side: Near 135B. Lower side: Near 141D.

*Size.*—About 3-inches.

*Quantity.*—Numerous.

*Shape.*—Lanceolate.

*Texture.*—Smooth.

*Ribs.*—Central, keeled.

*Arrangement.*—Bi-lateral along stem.

*Stem color.*—Green.

Bud:

*Shape.*—Oval.

*Color.*—Green.

*Length.*—About $\frac{3}{4}$-inch.

*Diameter.*—About $\frac{1}{3}$-inch.

Calyx:

*Number of sepals.*—About 6.

*Length.*—About $\frac{1}{3}$-inch.

*Width.*—About $\frac{1}{4}$-inch.

*Color.*—Outside — near 144A. Inside — near 145D.

Bloom:

*Shape.*—Round.

*Size.*—Diameter average: About 1¾-inches. Depth average: About 1-inch.

*Borne.*—As a spray.

*Color.*—General tonality: Near 46D. Upper side: Near 46B. Lower side: Near 47B. Center: Near 45D. Outer petals: Near 46B.

*Keeping quality.*—3 to 4 weeks on plant.

*Fragrance.*—Slight.

Petals:

*Number.*—About 40.

*Outer petals.*—Length: About 1-inch. Width: About ¾-inch.

*Central petals.*—Length: About ½-inch. Width: About ¾-inch.

*Texture.*—Smooth.

*Form.*—Fan shaped.

*Appearance.*—Shiny.

Reproductive organs:

*Stamens.* 13 Number: About 16. Arrangement: Around the ovary.

*Anthers.*—Length: About 1/10-inch. Color: Near 164B.

*Filaments.*—Length: About ¾-inch. Color: Near to 164B.

*Pistil.*—Number: About 4. Color: Near 186D. Length: About 1-inch.

*Stigma.*—Number: About 4. Color: Near 182D.

*Ovary.*—Shape: Conical. Color: Body — green. Apex — tannish green.

*Fertility.*—Female — fair. Male — excellent.

I claim:

1. A new and distinct dwarf variety of carnation plant named 'CFPC Fresco', substantially as shown and described.

* * * * *

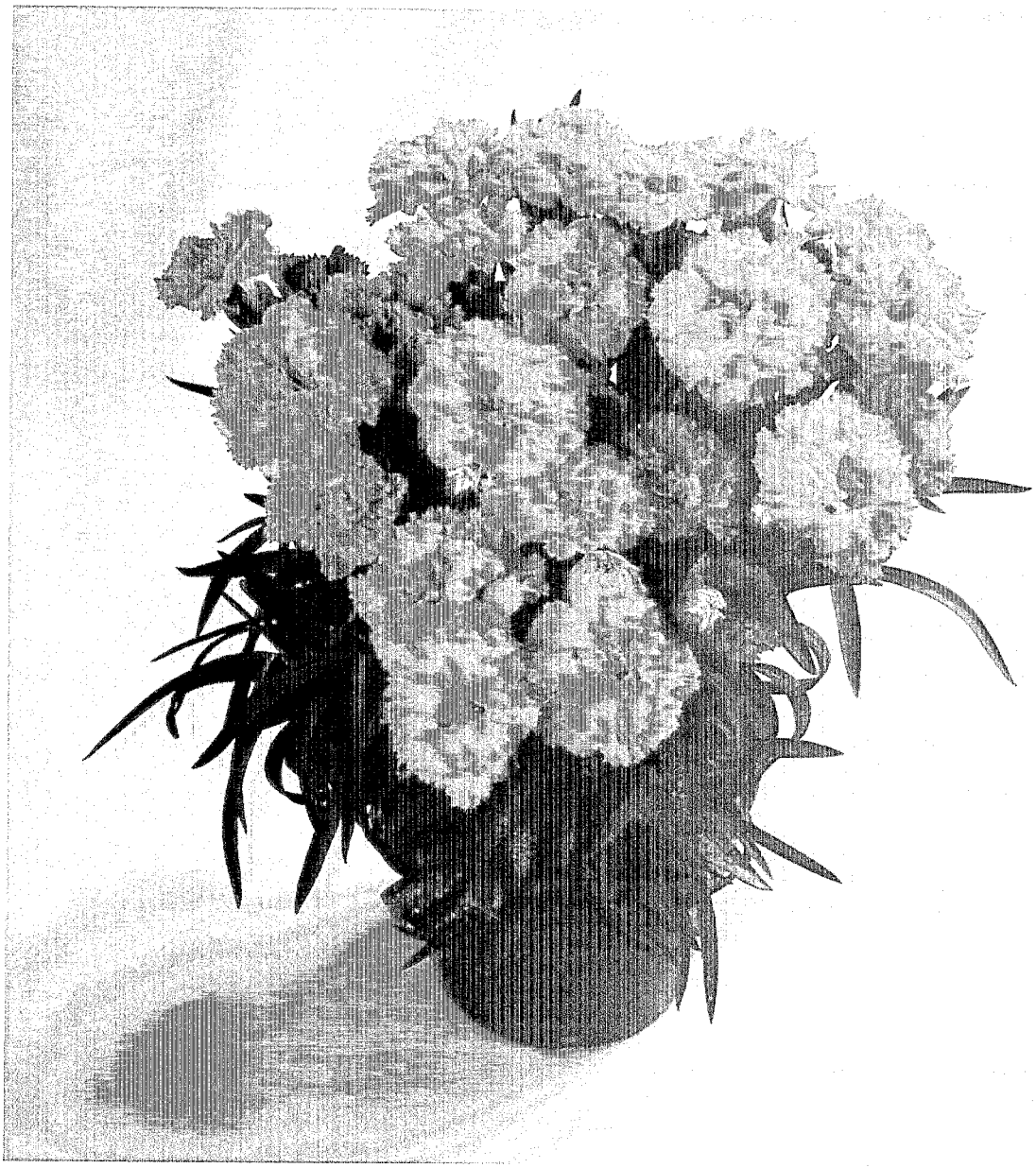

UNITED STATES PATENT AND TRADEMARK OFFICE

CERTIFICATE OF CORRECTION

PATENT NO. : Plant 9,269

DATED : August 29, 1995

INVENTOR(S) : Walter H. Jessel, Jr.

It is certified that error appears in the above-indentified patent and that said Letters Patent is hereby corrected as shown below:

Column 1, line 48, change "Horitcultural" to -- Horticultural --.

Column 2, line 19, change "seeding" to "seedling".

Column 4, line 3, after "*Stamens.*" delete "13".

Signed and Sealed this

Thirteenth Day of February, 1996

*Attest:*

BRUCE LEHMAN

*Attesting Officer*

*Commissioner of Patents and Trademarks*